(12) United States Patent
Suresh et al.

(10) Patent No.: US 10,702,843 B2
(45) Date of Patent: Jul. 7, 2020

(54) COMPOSITIONS OF MATTER COMPRISING SUSPENDED NANOPARTICLES AND RELATED METHODS

(71) Applicant: Baker Hughes, a GE company, LLC, Houston, TX (US)

(72) Inventors: Radhika Suresh, Sugar Land, TX (US); Devesh K. Agrawal, Houston, TX (US); Oleksandr V. Kuznetsov, Manvel, TX (US); Oleg A. Mazyar, Katy, TX (US); Valery N. Khabashesku, Houston, TX (US); Qusai Darugar, Houston, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 47 days.

(21) Appl. No.: 15/940,459

(22) Filed: Mar. 29, 2018

(65) Prior Publication Data
US 2019/0299184 A1    Oct. 3, 2019

(51) Int. Cl.
| | | |
|---|---|---|
| *B01J 13/00* | (2006.01) |
| *C09K 8/57* | (2006.01) |
| *C09K 8/06* | (2006.01) |
| *C09K 8/70* | (2006.01) |
| *C09K 8/66* | (2006.01) |
| *C09D 17/00* | (2006.01) |

(Continued)

(52) U.S. Cl.
CPC ........ *B01J 13/0047* (2013.01); *C09D 17/001* (2013.01); *C09D 17/007* (2013.01); *C09K 8/06* (2013.01); *C09K 8/572* (2013.01); *C09K 8/58* (2013.01); *C09K 8/665* (2013.01); *C09K 8/70* (2013.01); *E21B 21/00* (2013.01); *E21B 43/16* (2013.01); *E21B 43/26* (2013.01); *B82Y 5/00* (2013.01); *B82Y 25/00* (2013.01); *B82Y 30/00* (2013.01); *B82Y 40/00* (2013.01); *C09K 2208/10* (2013.01); *Y10S 977/774* (2013.01); *Y10S 977/811* (2013.01); *Y10S 977/896* (2013.01)

(58) Field of Classification Search
None
See application file for complete search history.

(56) References Cited

U.S. PATENT DOCUMENTS

| | | |
|---|---|---|
| 6,548,264 B1 | 4/2003 | Tan et al. |
| 7,129,277 B2 | 10/2006 | Baran, Jr. |

(Continued)

OTHER PUBLICATIONS

Azadgoleh et al., Stability of Silica Nanoparticle Dispersion in Brine Solution: an Experimental Study, Iranian Journal of Oil & Gas Science and Technology, vol. 3, No. 4, (2014), pp. 26-40.

(Continued)

*Primary Examiner* — John J Figueroa
(74) *Attorney, Agent, or Firm* — TraskBritt

(57) ABSTRACT

A composition of matter includes a liquid and nanoparticles suspended in the liquid. The nanoparticles each include silica, alumina, and an organosilicon functional group having a molecular weight of at least 200. A method includes functionalizing a surface of nanoparticles with an organosilicon functional group and dispersing the nanoparticles in a liquid to form a suspension. The functional group has a molecular weight of at least 200. The nanoparticles each include silica and alumina at a surface thereof.

20 Claims, 2 Drawing Sheets

(51) Int. Cl.
*E21B 21/00* (2006.01)
*E21B 43/16* (2006.01)
*E21B 43/26* (2006.01)
*C09K 8/58* (2006.01)
*B82Y 30/00* (2011.01)
*B82Y 40/00* (2011.01)
*B82Y 5/00* (2011.01)
*B82Y 25/00* (2011.01)

(56) References Cited

U.S. PATENT DOCUMENTS

| | | |
|---|---|---|
| 7,357,979 B2 | 4/2008 | Bringley et al. |
| 8,071,677 B2 | 12/2011 | Chen et al. |
| 8,541,322 B2 | 9/2013 | Barrera et al. |
| 8,617,306 B2 | 12/2013 | Lambert et al. |
| 8,653,187 B2 | 2/2014 | Butler et al. |
| 8,708,047 B2 | 4/2014 | Chakraborty et al. |
| 8,808,567 B2 | 8/2014 | Mazyar et al. |
| 8,840,693 B2 | 9/2014 | Chakraborty et al. |
| 8,840,803 B2 | 9/2014 | Mazyar et al. |
| 8,907,000 B2 | 12/2014 | Khabashesku et al. |
| 8,991,498 B2 | 3/2015 | Chakraborty et al. |
| 9,005,446 B2 | 4/2015 | Mazyar |
| 9,012,377 B2 | 4/2015 | Khabashesku et al. |
| 9,017,546 B2 | 4/2015 | Mazyar et al. |
| 9,120,978 B2 | 9/2015 | Mazyar et al. |
| 9,150,771 B2 | 10/2015 | Mazyar et al. |
| 9,228,420 B2 | 1/2016 | Mazyar et al. |
| 9,260,957 B2 | 2/2016 | Commarieu et al. |
| 9,283,619 B2 | 3/2016 | Mazyar et al. |
| 9,365,664 B2 | 6/2016 | Schmidt et al. |
| 9,580,658 B2 | 2/2017 | Kuznetsov et al. |
| 9,581,001 B2 | 2/2017 | Mazyar et al. |
| 9,611,422 B2 | 4/2017 | Suresh et al. |
| 9,611,699 B2 | 4/2017 | Chakraborty et al. |
| 9,683,163 B2 | 6/2017 | Mazyar et al. |
| 9,708,525 B2 | 7/2017 | Suresh et al. |
| 9,708,896 B2 | 7/2017 | Suresh et al. |
| 9,816,026 B2 | 11/2017 | Mazyar et al. |
| 9,833,838 B2 | 12/2017 | Mazyar et al. |
| 9,840,669 B2 | 12/2017 | Kuznetsov et al. |
| 9,856,158 B2 | 1/2018 | Mazyar et al. |
| 9,873,827 B2 | 1/2018 | Chakraborty et al. |
| 9,879,511 B2 | 1/2018 | Mazyar et al. |
| 9,885,226 B2 | 2/2018 | Mazyar et al. |
| 9,902,896 B2 | 2/2018 | Agrawal et al. |
| 2010/0314108 A1 | 12/2010 | Crews et al. |
| 2011/0081494 A1 | 4/2011 | Khabashesku et al. |
| 2012/0004342 A1 | 1/2012 | Lambert et al. |
| 2012/0052038 A1 | 3/2012 | Panandiker et al. |
| 2013/0084643 A1* | 4/2013 | Commarieu ............ C09K 8/03 436/27 |
| 2013/0112911 A1 | 5/2013 | Mazyar et al. |
| 2013/0165353 A1 | 6/2013 | Mazyar et al. |
| 2013/0200299 A1 | 8/2013 | Mazyar et al. |
| 2013/0334098 A1 | 12/2013 | Mazyar et al. |
| 2013/0334100 A1 | 12/2013 | Mazyar et al. |
| 2014/0000898 A1 | 1/2014 | Chakraborty et al. |
| 2014/0005304 A1 | 1/2014 | Suresh et al. |
| 2014/0027116 A1 | 1/2014 | Suresh et al. |
| 2014/0187449 A1 | 7/2014 | Khabashesku et al. |
| 2015/0008048 A1 | 1/2015 | Chakraborty et al. |
| 2015/0047841 A1 | 2/2015 | Mazyar et al. |
| 2015/0093589 A1 | 4/2015 | Mazyar et al. |
| 2015/0144343 A1 | 5/2015 | Mazyar et al. |
| 2015/0144344 A1 | 5/2015 | Mazyar et al. |
| 2015/0191646 A1 | 7/2015 | Mazyar et al. |
| 2015/0218435 A1 | 8/2015 | Suresh et al. |
| 2015/0218921 A1 | 8/2015 | Suresh et al. |
| 2015/0344769 A1 | 12/2015 | Suresh et al. |
| 2015/0344786 A1 | 12/2015 | Kuznetsov et al. |
| 2015/0353836 A1 | 12/2015 | Kuznetsov et al. |
| 2015/0361773 A1 | 12/2015 | Agrawal et al. |
| 2016/0017202 A1 | 1/2016 | Yang et al. |
| 2016/0348488 A1 | 12/2016 | Mazyar et al. |
| 2016/0369157 A1 | 12/2016 | Agrawal et al. |
| 2016/0376492 A1 | 12/2016 | Chakraborty et al. |
| 2017/0088696 A1 | 3/2017 | Dolog et al. |
| 2017/0137704 A1 | 5/2017 | Mazyar et al. |
| 2017/0210973 A1 | 7/2017 | Agrawal et al. |
| 2017/0247599 A1 | 8/2017 | Mazyar et al. |
| 2017/0327722 A1 | 11/2017 | Li et al. |
| 2017/0349461 A1 | 12/2017 | Kuznetsov et al. |
| 2017/0361376 A1 | 12/2017 | Murugesan et al. |
| 2018/0044580 A1 | 2/2018 | Mazyar et al. |
| 2018/0044595 A1 | 2/2018 | Mazyar et al. |
| 2018/0194947 A1 | 7/2018 | Lortz et al. |
| 2018/0312741 A1 | 11/2018 | Lortz et al. |
| 2019/0106328 A1 | 4/2019 | Lortz et al. |
| 2019/0127587 A1 | 5/2019 | Lortz et al. |

OTHER PUBLICATIONS

Bagaria et al., Adsorption of Iron Oxide Nanoclusters Stabilized with Sulfonated Copolymers on Silica in Concentrated NaCl and CaCl2 Brine, Journal of Colloid and Interface Science, vol. 398 (2013), pp. 217-226.

Bagaria et al., Iron Oxide Nanoparticles Grafted wit Sulfonated Copolymers are Stable in Concentrated Brine at Elevated Temperatures and Weakly Adsorb on Silica, Applied Materials and Interfaces, vol. 5, (2013), pp. 3329-3339.

Iqbal et al., High Temperature Stability and Low Adsorption of Sub-100 nm Magnitite Nanoparticles Grafted with Sulfonated Copolymers on Berea Sandstone in HIgh Salinity Brine, Colloids and Sufaces A: Physicochem. Eng. Aspects, vol. 520, (2017), pp. 257-267.

Metin et al., Stability of Aqueous Silica Nanoparticle Dispersons under Subsurface Conditions, Clean Technology, Clean Technology (2010), www.ct-si.org, ISBN 978-1-4398-3419-0. 25, pp. 25-28.

Metin et al., Stability of Aqueous Silica Nanoparticle Dispersions, J. Nanopart Res., vol. 13, (2011), pp. 839-850.

Worthen et al., Stoic Stabilization of Nanoparticles with Grafted Low Molecular Weight Ligands in Highly Concentrated Brines Including Divalent Ions, Soft Matter, vol. 12, (2016), pp. 2025-2039.

Xue et al., Effect of Grafted Copolymer Composition on Iron Oxide Nanoparticle Stability and Transport in Porous Media at High Salinity, Energy & Fuels, vol. 28, (2014), pp. 3655-3665.

International Search Report for International Application No. PCT/US2019/024680 dated Aug. 8, 2019, 5 pages.

International Written Opinion for International Application No. PCT/US2019/024680 dated Aug. 8, 2019, 6 pages.

Third Part Observation for International Application No. PCT/US2019/024680 dated Mar. 23, 2020, 4 pages.

* cited by examiner

COMPOSITIONS OF MATTER COMPRISING SUSPENDED NANOPARTICLES AND RELATED METHODS

FIELD

Embodiments of the present disclosure relate generally to suspensions of nanoparticles and methods of forming and using suspensions.

BACKGROUND

Nanoparticles are generally defined as particles having a diameter of less than 1 micron. Nanoparticles may be used in a variety of processes within the oil-and-gas industry, such as enhanced oil recovery, clay stabilization, drilling fluids, fracturing fluids, etc. Nanoparticles may also be used for products such as dyes and pigments, coatings, magnetic recording media, quantum dots, and semiconductors.

Nanoparticles may be used to form suspensions or colloids. There are certain challenges in forming and maintaining suspensions of nanoparticles. For example, particles tend to aggregate more quickly in liquids having higher ionic strengths, and aggregates tend to settle from the suspension.

Solid surfaces exposed to a liquid exhibit a structure referred to in the art as an electrical double layer, in which two layers of oppositely charged particles (e.g., ions and electrons) cover the surface. In the case of nanoparticles, the layers may surround the nanoparticles. As the size of the nanoparticles decreases, the effect of the charged layers on the nanoparticles' stability in the liquid increases. Furthermore, the size of the electrical double layer decreases as the ionic strength of the liquid increases. A decrease in the electrical double layer corresponds to a decrease in repulsive forces between nanoparticles. Because repulsive forces generally limit the rate of aggregation of nanoparticles, large ionic strengths of the liquid therefore allow attractive van der Waals forces between nanoparticles to dominate their movement, and dispersions of nanoparticles in high-ionic-strength liquids tend to become unstable and form sediment (i.e., larger agglomerations of particles that fall from the suspension). With an increase in temperature, the kinetic energy of suspensions increases, which leads to more frequent and higher-energy particle collisions, which further disrupt the electrical double layer and cause nanoparticles to aggregate.

Colloidal nanoparticle suspension may generally be controlled through charge stabilization, steric stabilization, or a combination of both charge and steric stabilization. Colloidal stability of nanoparticles is important for certain applications in aqueous media containing high electrolytes like biological fluids, sea water, high-brine concentrated injection fluids, etc. Many practical applications in biomedical, environmental, and oil and gas applications use high-ionic-strength liquids. In such applications, nanoparticle stability is crucial.

BRIEF SUMMARY

A composition of matter includes a liquid and nanoparticles suspended in the liquid. The nanoparticles each include silica, alumina, and an organosilicon functional group having a molecular weight of at least 200.

A method includes functionalizing a surface of nanoparticles with an organosilicon functional group and dispersing the nanoparticles in a liquid to form a suspension. The functional group has a molecular weight of at least 200. The nanoparticles each include silica and alumina at a surface thereof.

DETAILED DESCRIPTION

The illustrations presented herein are not actual views of any particular particle or suspension, but are merely idealized representations employed to describe example embodiments of the present disclosure. The following description provides specific details of embodiments of the present disclosure in order to provide a thorough description thereof. However, a person of ordinary skill in the art will understand that the embodiments of the disclosure may be practiced without employing many such specific details. Indeed, the embodiments of the disclosure may be practiced in conjunction with conventional techniques employed in the industry. In addition, only those process acts and structures necessary to understand the embodiments of the disclosure are described in detail below. Additional conventional acts and structures may be used. Also note, the drawings accompanying the application are for illustrative purposes only, and are not drawn to scale. Additionally, elements common between figures may have corresponding numerical designations.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features and methods usable in combination therewith should or must be excluded.

As used herein, the singular forms following "a," "an," and "the" are intended to include the plural forms as well, unless the context clearly indicates otherwise.

As used herein, the term "and/or" includes any and all combinations of one or more of the associated listed items.

As used herein, the term "about" used in reference to a given parameter is inclusive of the stated value and has the meaning dictated by the context (e.g., it includes the degree of error associated with measurement of the given parameter).

Figure 1:
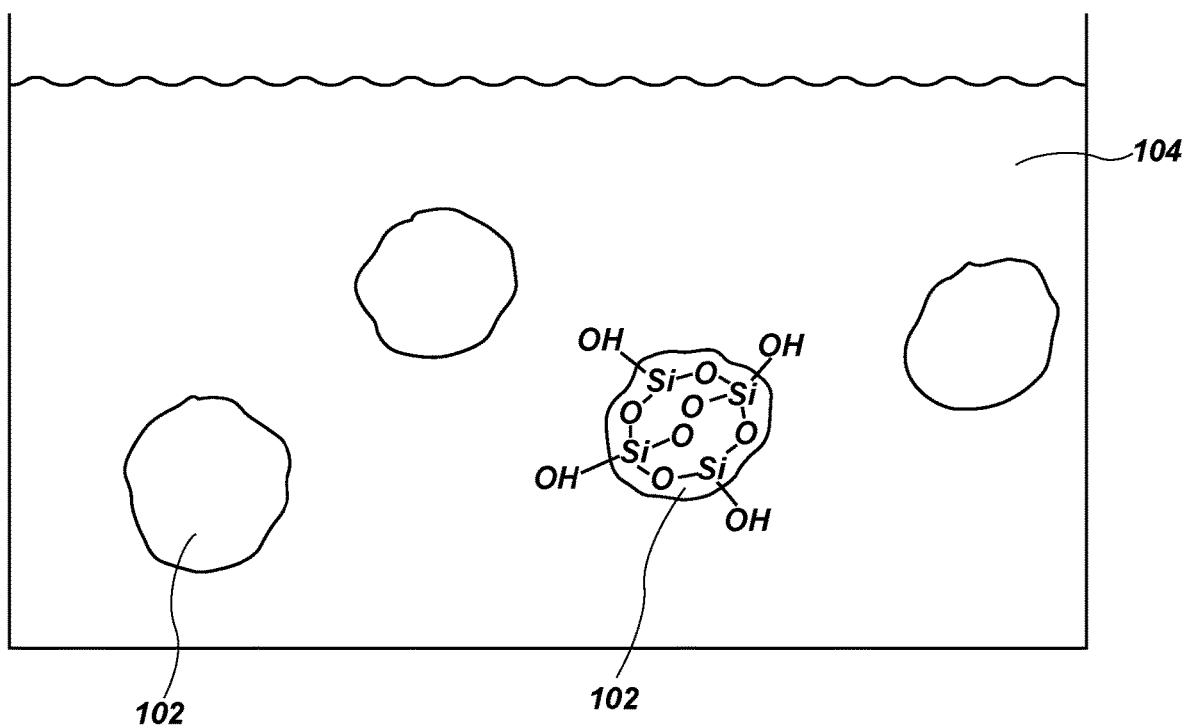
FIG. 1 is a simplified illustration showing a suspension of silica nanoparticles in a liquid.

FIG. 1 illustrates nanoparticles 102 of silica. The nanoparticles 102 may be suspended in a liquid 104. The liquid 104 may include an aqueous medium comprising water and at least one other component. For example, the liquid 104 may include a mixture of ethanol and water, one or more salts dissolved in water, etc. In some embodiments, the liquid 104 may be an aqueous brine, such as seawater. The liquid 104 may have dissolved divalent or other multivalent ions therein, such as $Mg^{2+}$, $Ca^{2+}$, $Sr^{2+}$, $Ba^{2+}$, $Fe^{2+}$, $Fe^{3+}$, $Cu^{2+}$, $CO_3^{2-}$, $SO_3^{2-}$, $SO_4^{2-}$, $S^{2-}$, $PO_4^{3-}$, etc. For example, the liquid may have at least about 10 parts per thousand (ppt) of dissolved salts, at least about 20 ppt of dissolved salts, or even at least about 30 ppt of dissolved salts. In certain embodiments, the liquid 104 may include a glycol (e.g., ethylene glycol) or a mixture of solvents, such as tetrahydrofuran, dimethylformamide, dimethyl sulfoxide, propylcarbonate, acetone, acetate, toluene, etc.

Figure 2:
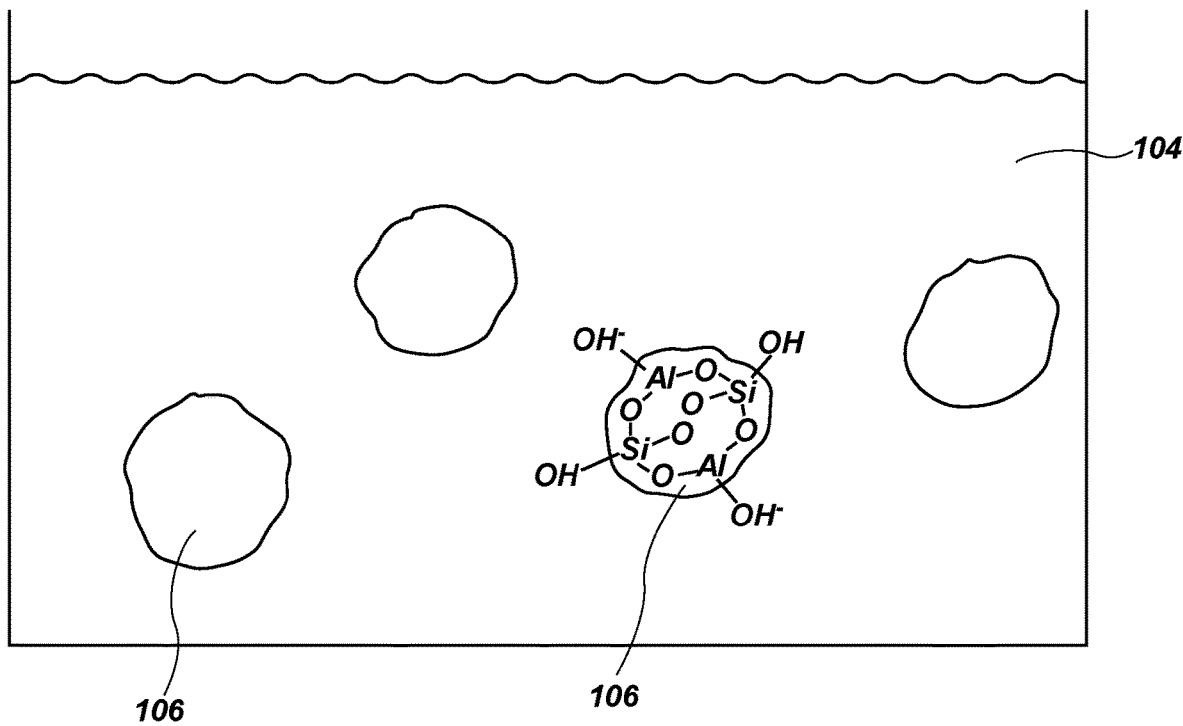
FIG. 2 is a simplified illustration showing a suspension of nanoparticles of silica and alumina in a liquid.

Hydroxyl (—OH) groups may be attracted to silicon atoms at the surfaces of the nanoparticles 102 by van der Waals forces, forming silanol (Si—OH) functional groups on the surfaces of the nanoparticles 102. The exposed surface of the nanoparticles 102 may be modified to substitute at least some silicon atoms with aluminum, forming the nanoparticles 106 shown in FIG. 2. The surfaces of the nanoparticles 106 may include both Si—OH and Al—OH groups. Al—OH groups are more basic as compared to Si—OH groups. By substituting at least some silicon atoms with aluminum atoms, the nanoparticles 106 may be generally more chemically stable than the nanoparticles 102 of FIG. 1.

Figure 3:
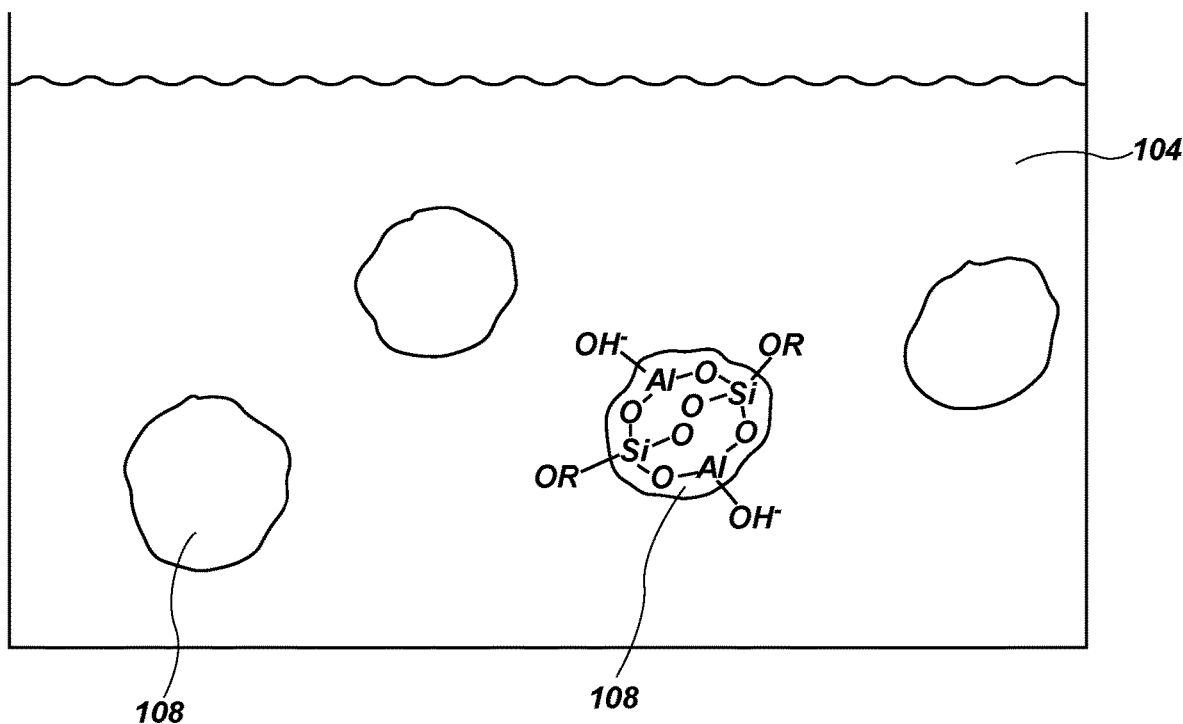
FIG. 3 is a simplified illustration showing a suspension of functionalized nanoparticles of silica and alumina in a liquid.

The nanoparticles 106 may be functionalized by bonding a functional group R to silicon atoms thereof to form functionalized nanoparticles 108, as shown in FIG. 3. The functional group R may be an organosilicon functional group having a silicon atom and at least one organic moiety connected by a Si—C bond. The functional group R may provide steric stabilization to the functionalized nanoparticles 108, and may make the functionalized nanoparticles 108 relatively more physically stable in a suspension of the liquid 104. The functional group R may have a molecular weight (MW) of at least 200. The size and molecular weight of the functional group R may influence the stabilizing and steric effect on the nanoparticles 108. In some embodiments, the functional group R may be formed from any of the compounds listed and shown in Table 1 or any of the classes of compounds listed in Table 2.

TABLE 1

| Name | MW | Structure |
|---|---|---|
| (3-glycidyloxypropyl) trimethoxysilane (also known as GLYMO) | 236 | 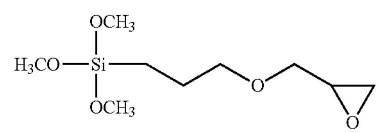 [SMILES: CO[Si](CCCOCC1CO1)(OC)OC] |
| 3-(trimethoxysilyl)propyl acrylate | 234 | 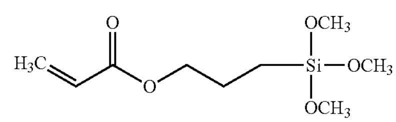 |
| 3-(trimethoxysilyl)propyl methacrylate | 248 | 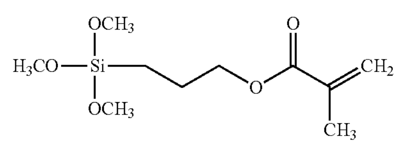 [SMILES: C=C(C)C(=O)OCCC[Si](OC)(OC)OC] |
| trimethoxy(octadecyl)silane | 375 | 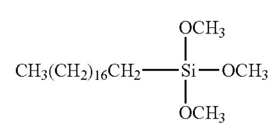 |
| hexadecyltrimethoxysilane | 347 | 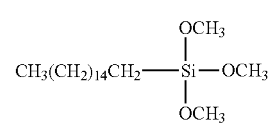 |
| trimethoxy(7-octen-1-yl)silane | 232 | 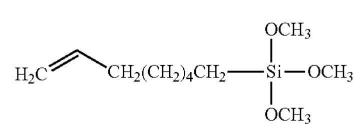 |

TABLE 2

| Description | Structure |
|---|---|
| methoxy PEG silane | H₃CO–(–O–)ₙ–C(=O)–NH–CH₂CH₂CH₂–Si(OCH₂CH₃)₃ |
| carboxylic acid terminated PEG silane | (CH₃CH₂O)₃Si–CH₂CH₂NHC(=O)NH–CH₂CH₂–(OCH₂CH₂)ₙ–COOH |
| amine terminated PEG silane | (CH₃CH₂O)₃Si–CH₂CH₂NHC(=O)NH–CH₂CH₂–(OCH₂CH₂)ₙ–NH₂ |
| O-[methoxy(polyethylene oxide)]-n-triethoxysilylpropyl) carbamate | CH₃O–(–O–)₁₅₋₂₀–C(=O)–NH–CH₂CH₂CH₂–Si(OEt)₃ |
| 2-[methoxypoly(ethylenoxy)6-9propyl]dimethylmethoxysilane | CH₃O–(–O–)₆₋₉–CH₂CH₂CH₂–Si(CH₃)₂–OCH₃ |
| 2-[methoxy(polyethyleneoxy)6-9propyl]trichlorosilane | CH₃O–(–O–)₆₋₉–CH₂CH₂CH₂–SiCl₃ |
| 2-[methoxypoly(ethylenoxy)6-9propyl]dimethylchlorosilane | CH₃O–(–O–)₆₋₉–CH₂CH₂CH₂–Si(CH₃)₂–Cl |
| [hydroxy(polyethyleneoxy)propyl]triethoxysilane | HO–(–O–)₈₋₁₂–CH₂CH₂CH₂–Si(OEt)₃ |

In some embodiments, the functional group R may include a glucose, sucrose-, or fructose-modified silane or siloxane. The functional group R may include an alkoxy group (i.e., an alkyl group singularly bonded to oxygen) bonded to silicon. Without being bound to any particular theory, it appears that such an alkoxy group aids in the formation of a covalent bond to silicon atoms at the surfaces of the nanoparticles 106. The functional group R may be hydrophilic to improve the suspension of the functionalized nanoparticles 108 in water. Each functionalized nanoparticle 108 may include one or more functional groups R bonded thereto. The degree of stability of the functionalized nanoparticles 108 may increase with an increasing number of functional groups R.

To bond the functional groups R with silicon atoms at the surfaces of the nanoparticles 106, the functional groups R may be added to the liquid 104 containing the nanoparticles 106, and the mixture may be heated to a reaction temperature, though the reaction may proceed even without heating. For example, if the functional group R is GLYMO, the mixture may be heated to a temperature of at least about 50° C., at least about 60° C., or at least about 65° C., and the reaction rate may vary based on temperature. The functional groups R may replace —OH groups bonded to the surfaces of the nanoparticles 106. In some embodiments, functional groups R may be bonded to each exposed silicon atom, such that the only —OH groups attached directly to the surfaces of nanoparticles 108 are bonded to aluminum atoms.

Suspensions of the functionalized nanoparticles 108 may exhibit increased stability with respect to suspensions of unfunctionalized nanoparticles 106. For example, at least 50%, at least 75%, or even at least 90% of the functionalized nanoparticles 108 may remain in suspension in the liquid 104 when the suspension is maintained at a temperature of 30° C. for 30 days. At least 50%, at least 75%, or even at least 90% of the functionalized nanoparticles 108 may remain in suspension in the liquid 104 when the suspension is maintained at a temperature of 70° C. for 10 days. At least 50%, at least 75%, or even at least 90% of the functionalized nanoparticles 108 may remain in suspension in the liquid 104 when the suspension is maintained at a temperature of 90° C. for 24 hours. In comparison, a majority of unfunctionalized nanoparticles 106 may precipitate out of the liquid 104 when the suspension thereof is maintained at the same temperatures for the same time periods.

Furthermore, because the functionalized nanoparticles 108 have fewer Si—OH bonds, dehydration may be decreased with respect to conventional nanoparticles. This may increase the chemical stability of the functionalized nanoparticles 108, increasing the time period before the functionalized nanoparticles 108 degrade at a selected temperature. This effect may be particularly important in liquids 104 having high ionic strength. For example, liquids 104 with divalent ions may tend to readily dehydrate Si—OH bonds, but may not react with silica atoms functionalized with the functional groups R as quickly.

Without being bound by any particular theory, it appears that improved stability of the nanoparticles 108 in the liquid 104 may be associated with the neutralization of the overall charge of the core of the nanoparticles 108. Dissociation of acidic —SiOH groups with the release of protons leaves negatively charged sites on the nanoparticle 108, while the dissociation of —AlOH may result either in $OH^-$ or $H^+$ products. It appears that the primary dissociation route of —AlOH in presence of —SiOH groups is the production of $OH^-$ groups, which tends to maintain the pH of the liquid 104. Remaining positive charges on aluminum atoms and negative charges on the outermost oxygen atoms attached to silicon atoms may tend to maintain the overall charge of the nanoparticles 108 near zero. Ions in the liquid 104 may either form alternating-charge shells ("+" near the negatively charged sites on the nanoparticles 108 and "–" near the positively charged sites on the nanoparticles 108) or not form the structured shells at all. Charge-neutral nanoparticles 108 may be less likely to interact with one another.

The presence of the functional groups R may provide steric hindrance to further interactions, even if some of the functional groups R become hydroxylated. Furthermore, functionalization of the nanoparticles 108 may decrease the number of silanol groups available for dehydration.

The suspension of the nanoparticles 108 may be used in a wide variety of applications. For example, the suspension may be injected into a subterranean well for enhanced oil recovery, clay stabilization, drilling fluids, fracturing fluids, etc., in the oil-and-gas industry. The suspension may also be used to form dyes and pigments, coatings, magnetic recording media, quantum dots, and semiconductors. In some embodiments, the suspension may be a biological fluid, such as blood or a component thereof.

Example 1

Aluminosilicate nanoparticles having a mean particle diameter of about 25 nm were dispersed in a mixture of ethanol, water, and GLYMO. The mixture was heated to about 65° C. to functionalize the nanoparticles with the GLYMO. The functionalized nanoparticles were dispersed in simulated seawater having a total dissolved salt concentration of about 3.52% (35.2 ppt), as shown in Table 3, and samples thereof were separated and maintained at various elevated temperatures (60° C., 70° C., 80° C., and 90° C.) under static conditions. Over a period of 800 minutes (13.3 hours), no appreciable precipitation or settling of the functionalized nanoparticles occurred, even at the highest temperature.

TABLE 3

| Composition of Artificial Sea Water | |
|---|---|
| Salt | Weight % |
| NaCl | 2.3926 |
| $Na_2SO_4$ | 0.4008 |
| KCl | 0.0677 |
| $NaHCO_3$ | 0.0196 |
| KBr | 0.0098 |
| $H_3BO_3$ | 0.0026 |
| NaF | 0.0003 |
| $MgCl_2·6H_2O$ | 0.507823 |
| $CaCl_2·2H_2O$ | 0.114694 |
| $SrCl_2·6H_2O$ | 0.001428 |
| Total | 3.517 |

Example 2

Functionalized nanoparticles as formed in Example 1 were maintained at 80° C. for a period of 800 minutes, during which the mean particle diameter was measured using dynamic light scattering in a Zetasizer instrument, available from Malvern Instruments Limited, of Malvern, Worcestershire, UK. Over the course of the test, the mean particle diameter did not change by a statistically significant amount. This indicates that little aggregation of the nanoparticles occurred.

Example 3

Functionalized nanoparticles as formed in Example 1 were subjected to thermogravimetric analysis (TGA). The nanoparticles experienced a decomposition peak at a temperature of about 400° C., and lost about 17.9% of the mass of the particles at temperatures between 200° C. and 700° C. Non-functionalized aluminosilicate nanoparticles subjected to TGA experienced no such decomposition. TGA of neat GLYMO showed a decomposition peak at a temperature below 200° C., and nearly a total loss of mass between 100° C. and 400° C. The shift in the decomposition of the GLYMO from below 200° C. to about 400° C. suggests covalent attachment of the GLYMO to the aluminosilicate nanoparticles and/or changes in the structure of the GLYMO upon binding to the aluminosilicate nanoparticles.

Example 4

Functionalized nanoparticles in simulated seawater as formed in Example 1 were maintained at a temperature of 60° C. for 72 days, after which the samples were observed to determine whether the nanoparticles had precipitated. After 72 days, the functionalized nanoparticles had not precipitated, indicating that the suspension was stable for that time and temperature. Each sample of colloidal silica nanoparticles had settled to the bottom of the vials, indicating that the suspensions were unstable under those conditions.

Comparative Example 5

Commercially available colloidal silica nanoparticles were dispersed in simulated seawater and maintained at temperatures of 70° C. and 80° C. The nanoparticles included NYACOL® DP9711, available from Nyacol Nano Technologies, Inc., of Ashland Mass.; OFC12 and SNOWTEX® ST-XS, available from Nissan Chemical America Corporation, of Houston, Tex.; Levasil CB25, Levasil CB25A, and Levasil CC301, and Levasil CC401 each available from AkzoNobel, of Amsterdam, the Netherlands; and AEROSIL® 300, available from Evonik Industries AG, of Essen, Germany. A sample of the AEROSIL® 300 nanoparticles was functionalized with GLYMO, as described in Example 1. Another sample of the AEROSIL® 300 nanoparticles was dispersed in simulated seawater with a pH of about 9.

Over a period of 800 minutes (13.3 hours), each sample of colloidal silica nanoparticles had settled to the bottom of the vials, indicating that the suspensions were unstable at 70° C. and 80° C.

Additional non-limiting example embodiments of the disclosure are described below.

Embodiment 1

A composition of matter, comprising a liquid and nanoparticles suspended in the liquid. The nanoparticles each comprise silica, alumina, and an organosilicon functional group having a molecular weight of at least 200.

Embodiment 2

The composition of Embodiment 1, wherein the organosilicon functional group comprises (3-glycidyloxypropyl) trimethoxysilane.

Embodiment 3

The composition of Embodiment 1 or Embodiment 2, wherein the liquid comprises aqueous brine.

Embodiment 4

The composition of Embodiment 3, wherein the liquid comprises seawater.

Embodiment 5

The composition of Embodiment 3, wherein the liquid comprises dissolved multivalent ions.

Embodiment 6

The composition of Embodiment 5, wherein the dissolved multivalent ions are selected from the group consisting of $Mg^{2+}$, $Ca^{2+}$, $Sr^{2+}$, $Ba^{2+}$, $Fe^{2+}$, $Fe^{3+}$, $Cu^{2+}$, $CO_3^{2-}$, $SO_3^{2-}$, $SO_4^{2-}$, $S^{2-}$, and $PO_4^{3-}$.

Embodiment 7

The composition of any of Embodiments 1 through 6, wherein the liquid comprises a glycol.

Embodiment 8

The composition of any of Embodiments 1 through 7, wherein at least 90% of the nanoparticles remain suspended in the liquid over a time period of 30 days at 30° C.

Embodiment 9

The composition of any of Embodiments 1 through 8, wherein at least 90% of the nanoparticles remain suspended in the liquid over a time period of 10 days at 70° C.

Embodiment 10

The composition of any of Embodiments 1 through 9, wherein at least 90% of the nanoparticles remain suspended in the liquid over a time period of 24 hours at 90° C.

Embodiment 11

A method, comprising functionalizing a surface of nanoparticles with an organosilicon functional group and dispersing the nanoparticles in a liquid to form a suspension. The functional group has a molecular weight of at least 200. The nanoparticles each comprise silica and alumina at a surface thereof.

Embodiment 12

The method of Embodiment 11, wherein functionalizing a surface of nanoparticles with an organosilicon functional group having a molecular weight of at least 200 comprises functionalizing the surface of nanoparticles with (3-glycidyloxypropyl)trimethoxysilane (GLYMO).

Embodiment 13

The method of Embodiment 11 or Embodiment 12, wherein dispersing the nanoparticles in a liquid comprises dispersing the nanoparticles in an aqueous medium.

Embodiment 14

The method of any of Embodiments 11 through 13, further comprising modifying an exposed surface of silica nanoparticles to form the nanoparticles comprising silica and aluminum.

Embodiment 15

The method of Embodiment 14, wherein modifying an exposed surface of silica nanoparticles comprises replacing a silanol group with Al—OH.

Embodiment 16

The method of any of Embodiments 11 through 15, wherein functionalizing a surface of nanoparticles with an organosilicon functional group comprises reacting the nanoparticles with the organosilicon functional group in the presence of ethanol and water.

Embodiment 17

The method of any of Embodiments 11 through 16, wherein functionalizing a surface of nanoparticles with an organosilicon functional group comprises reacting the nanoparticles with the organosilicon functional group in the presence of an organic solvent.

Embodiment 18

The method of Embodiment 17, wherein reacting the nanoparticles with the organosilicon functional group in the presence of an organic solvent comprises reacting the nanoparticles with the organosilicon functional group in the presence of at least one organic solvent selected from the group consisting of a glycol, tetrahydrofuran, dimethylformamide, dimethyl sulfoxide, propylcarbonate, acetone, acetate, and toluene.

Embodiment 19

The method of any of Embodiments 11 through 18, wherein functionalizing a surface of nanoparticles with an organosilicon functional group comprises reacting the nanoparticles with the organosilicon functional group at a temperature of at least 50° C.

Embodiment 20

The method of any of Embodiments 11 through 19, wherein functionalizing a surface of nanoparticles with an organosilicon functional group comprises bonding the organosilicon functional group with silicon atoms of the nanoparticles.

Embodiment 21

The method of any of Embodiments 11 through 20, further comprising injecting the suspension into a subterranean well.

Embodiment 22

The method of any of Embodiments 11 through 21, further comprising maintaining the suspension at a temperature of at least 30° C. for a time period of at least 30 days while maintaining at least 90% of the nanoparticles in the suspension.

While the present invention has been described herein with respect to certain illustrated embodiments, those of ordinary skill in the art will recognize and appreciate that it is not so limited. Rather, many additions, deletions, and modifications to the illustrated embodiments may be made without departing from the scope of the invention as claimed, including legal equivalents thereof. In addition, features from one embodiment may be combined with features of another embodiment while still being encompassed within the scope of the invention as contemplated by the inventors. Further, embodiments of the disclosure have utility with different and various processes and systems.

What is claimed is:

1. A composition of matter, comprising:
    a liquid; and
    nanoparticles suspended in the liquid, the nanoparticles each comprising:
        silica;
        alumina;
        organosilicon functional groups bonded to silicon atoms of the silica, none of the organosilicon functional groups of the nanoparticles being bonded to aluminum atoms of the alumina; and
        hydroxyl (—OH) groups bonded to the aluminum atoms of the alumina.

2. The composition of claim 1, wherein the liquid comprises aqueous brine.

3. The composition of claim 2, wherein the liquid comprises dissolved multivalent ions.

4. The composition of claim 3, wherein the dissolved multivalent ions are selected from the group consisting of $Mg^{2+}$, $Ca^{2+}$, $Sr^{2+}$, $Ba^{2+}$, $Fe^{2+}$, $Fe^{3+}$, $Cu^{2+}$, $CO_3^{2-}$, $SO_3^{2-}$, $SO_4^{2-}$, $S^{2-}$, and $PO_4^{3-}$.

5. The composition of claim 1, wherein the liquid comprises a glycol.

6. The composition of claim 1, wherein at least 90% of the nanoparticles remain suspended in the liquid over a time period of 30 days at 30° C.

7. The composition of claim 1, wherein at least 90% of the nanoparticles remain suspended in the liquid over a time period of 10 days at 70° C.

8. The composition of claim 1, wherein at least 90% of the nanoparticles remain suspended in the liquid over a time period of 24 hours at 90° C.

9. The composition of claim 1, wherein an organosilicon functional group of the organosilicon functional groups exhibits a molecular weight of at least 200.

10. A composition of matter, comprising:
    a liquid; and
    nanoparticles suspended in the liquid, the nanoparticles each comprising silica, alumina, and an organosilicon functional group, the organosilicon functional group comprising (3-glycidyloxypropyl)trimethoxysilane.

11. A method, comprising:
    functionalizing nanoparticles with an organosilicon functional group, the nanoparticles each comprising:
        silica;
        alumina;
        organosilicon functional groups bonded to silicon atoms of the silica, none of the organosilicon functional groups of the nanoparticles being bonded to aluminum atoms of the alumina; and
        hydroxyl (—OH) groups bonded to the aluminum atoms of the alumina; and
    forming a suspension of the nanoparticles in a liquid.

12. The method of claim 11, wherein functionalizing nanoparticles with an organosilicon functional group comprises functionalizing the nanoparticles with (3-glycidyloxypropyl)trimethoxysilane (GLYMO).

13. The method of claim 11, wherein forming a suspension of the nanoparticles in a liquid comprises dispersing the nanoparticles in an aqueous medium.

14. The method of claim 11, further comprising modifying an exposed surface of silica nanoparticles to form the nanoparticles comprising the silica and the alumina.

15. The method of claim 14, wherein modifying an exposed surface of silica nanoparticles comprises replacing a silanol group with Al—OH.

16. The method of claim 11, wherein functionalizing nanoparticles with an organosilicon functional group comprises reacting the nanoparticles with the organosilicon functional group in the presence of ethanol and water.

17. The method of claim 11, wherein functionalizing nanoparticles with an organosilicon functional group comprises reacting the nanoparticles with the organosilicon functional group at a temperature of at least 50° C.

18. The method of claim 11, wherein functionalizing nanoparticles with an organosilicon functional group comprises bonding the organosilicon functional group with the silicon atoms of the silica of the nanoparticles.

19. The method of claim 11, further comprising injecting the suspension into a subterranean well.

20. The method of claim 11, further comprising maintaining the suspension at a temperature of at least 30° C. for a time period of at least 30 days while maintaining at least 90% of the nanoparticles in the suspension.

* * * * *